(12) United States Patent
Hammer et al.

(10) Patent No.: US 7,399,621 B2
(45) Date of Patent: Jul. 15, 2008

(54) GENES CONFERRING HERBICIDE RESISTANCE

(75) Inventors: Philip E. Hammer, Cary, NC (US); Nicholas B. Duck, Apex, NC (US)

(73) Assignee: Athenix Corporation, Research Triangle Park, NC (US)

( * ) Notice: Subject to any disclaimer, the term of this patent is extended or adjusted under 35 U.S.C. 154(b) by 46 days.

(21) Appl. No.: 11/517,991

(22) Filed: Sep. 8, 2006

(65) Prior Publication Data

US 2007/0004907 A1 Jan. 4, 2007

Related U.S. Application Data

(62) Division of application No. 10/739,610, filed on Dec. 18, 2003.

(60) Provisional application No. 60/434,789, filed on Dec. 18, 2002.

(51) Int. Cl.
*C12N 9/10* (2006.01)
(52) U.S. Cl. ........................................ 435/193
(58) Field of Classification Search .................. None
See application file for complete search history.

(56) References Cited

U.S. PATENT DOCUMENTS

| 4,535,060 | A | 8/1985 | Comai |
| 4,769,061 | A | 9/1988 | Comai |
| 4,971,908 | A | 11/1990 | Kishore et al. |
| 5,094,945 | A | 3/1992 | Comai |
| 5,627,061 | A | 5/1997 | Barry et al. |
| 7,214,535 | B2 * | 5/2007 | Sun et al. ............ 435/419 |

FOREIGN PATENT DOCUMENTS

| EP | 0 389 066 B1 | 9/1990 |
| WO | WO 03/095649 A1 | 11/2003 |

OTHER PUBLICATIONS

Guo, H.H., et al., "Protein Tolerance to Random Amino Acid Change," *Proc Natl Acad Sci U.S.A.*, Jun. 22, 2004, pp. 9205-9210, vol. 101, No. 25.

Hiatt, W., et al., "Introduction and Expression in Plants of a Glyphosate Resistant *aroA* Gene Isolated from *Salmonella typhimurium*," *NATO Asi Series A. Life Sciences*, 1984, pp. 479-488, vol. 83.

Richmond, T.A., and C. R. Somerville, "The Cellulose Synthase Superfamily," *Plant Physiol.*, Oct. 1, 2000, pp. 495-498, vol. 124, No. 2.

Schmitt, E., et al., "Cloning of the *aro*A Gene from a Highly Resistant Glyphosate Degrading *Pseudomonas-sp.*," 1985, p. 192, vol. 85, Abstract.

Sost, D. and N. Amrhein, "Substitution of Gly-96 to Ala in the 5-Enolpyruvylshikimate 3-Phosphate Synthase of *Klebsiella pneumoniae* Results in a Greatly Reduced Affinity for the Herbicide Glylphosate," *Archives of Biochemistry and Biophysics*, 1990, pp. 433-436, vol. 282(2).

Stalker, D., et al., "A Single Amino Acid Substitution in the Enzyme 5 Enolypyruvylshikimate-3-phosphate Synthase Confers Resistance to the Herbicide Glyphosate," *The Journal of Biological Chemistry*, 1985, pp. 4724-4728, vol. 260(8).

Ye, G-N., et al., "Plastid-expressed 5-enolpyruvylshikimate-3-phosphate Synthase Genes Provide High Level Glyphosate Tolerance in Tobacco," *The Plant Journal*, 2001, pp. 261-270, vol. 25, No. 3.

* cited by examiner

*Primary Examiner*—Elizabeth Slobodyansky
(74) *Attorney, Agent, or Firm*—Alston & Bird LLP

(57) ABSTRACT

Compositions and methods for conferring herbicide resistance to plants, plant cells, tissues and seeds are provided. Compositions comprising a coding sequence for a polypeptide that confers resistance or tolerance to glyphosate herbicides are provided. The coding sequences can be used in DNA constructs or expression cassettes for transformation and expression in plants. Compositions also comprise transformed plants, plant cells, tissues, and seeds. In particular, isolated nucleic acid molecules encoding glyphosate resistance proteins are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:2 or the nucleotide sequence set forth in SEQ ID NO:1.

2 Claims, 5 Drawing Sheets

Fig. 2A

```
                         *         20         *         40         *         60         *         80
GRG-1       : ----------VKVTIQPGDLTEILQSLASHESMQLACAARLVAKGISEIINPCHSMCDKAARDIVSRLEARLEDQPDGSL :  70
Aeropyrum_  : ---MVWLRAPDRVVVHPSTREPRVEALPSESYTLPMLFLSLLLARGRSVLRRPLVSMCTLASLNAVALLE------GKPRL :  71
Archaeoglo  : ---------MDVIVRKG-EIRPKAKPPASESYTLPAFIASLSP-SARLVNPLISELTISLLNACKRLEAALL-KKG--N :  66
Clostridiu  : ---------MNCVKINPCCLKELIKILPSESLGLPALICLALSEEELTLENISYSKLIKALCIGMSKLEALLIEDAKDNS :  71
Clostridiu  : ---------MKKVIITPSKLRESLIKILPSEMALLALICLSLSKGESVLSNIDFSELLIALMEGMKSLEANLKVEKDKLI :  71
Fusobacter  : ------MRNMIEKKIIKADRLVLELGTPLPLSEVLLEYLLASSLAKGISLILENISYSDLLIIALIRAMKGLLANLEKKDNYLL :  74
Halobacter  : MPWAALLACMHATLSPS-REWRRARALPLESYTELALLALCYADGELVLRDPIVSALLTRALLARAVELLECAAA-REN--G :  76
Methanococ  : ---------MYLLIVRKTDRLELIEKALPLESYTLPALICLSLADCVSRLINPLWGALCLSLVHGCRMLLANLE-LDKKKD :  71
Methanopyr  : ---------MKRVELEGIPELRELTVCPLPSELGSLELALIALSLCDGSLELWNVLDAELVRALLRLCRMLLEARLEDVDGEERL :  72
Methanosar  : ---------MRASISKS-SLKPELVFALPSLESYTLEALTLEALSK-RSLELHRPLLSALLTLALIRASEMFLAALR-REK--E :  66
Methanosar  : ---------MRVSISKS-SLKPELVFALPSLESYTLEALTLEALSN-ESLELRRPLLSALLTLALIRASEMFLEASLK-REK--E :  66
Methanothe  : ---------MDLTVEKSGNLEETLKALPLESYTLPALIILALAEGVSLEIRDPLIAELTLSLLNACRAFLEIRLD-EG---D :  67
ARoA-Ecoli  : --------MESLTLQPIARLDLTLNLPLGSLTVSMLPALLLALAHGKLVLTNLLDSDLLVRHMLNALTALLEVSYTLSADRTR :  72
Bacillus_S  : ----------MKRDKVQTLHPELEHILGDELEISLLLSLMFGALLAACTLTLELNFLPGALLCLSLLIDCPRKLPVHLEQSSS--D :  67
AROA_AGRSP  : --MSHCASSRPATARKSSGLLSLELTLRILGDELIELALSFMFGGLLASGELLRMLTGLLLEGELVINLLCKAMQALLEARLLRKEGDTWI :  78
```

```
                         *        100         *        120         *        140         *        160
GRG-1       : QITSEG--VKPVALP--FLELCGELCLSLIELMFTPLVALSKEEVTLGK-ESGSLVTLLEDFFDEILPHLGVKVKSNQGK----L : 141
Aeropyrum_  : GRCVLAEVECGEVRCCAVLYAACLGLTLILIAMG-AA-HSAEATLLYGDESLLWNRLEVHPLSBALRSHGARVCDTGGN-----P : 146
Archaeoglo  : EWLPSGVDG--VEAHGYFLPANLGLTTLIFTGLLS-ESPPRSLVDLPDESLLRKLLENGELVLALESKLGARFHGREP---YTP : 140
Clostridiu  : TLKIKKQ-KLVSKEKVYLELCSELELSLTVLFLIPLSL-ELEERNVLFDLPQGKLESYPLLDSYFNIFDEKEIAYSHPEGK---VL : 146
Clostridiu  : INGKN---ILKDSNYKFLLDCNELSLGSTLLFLVPLSL-ELKDNRVNFIELRGNLLGKPLLLKTYYEIFEEQBIKYSYEE-E---NL : 143
Fusobacter  : IDGSKTFDKEYLNNDSELLDCNELSLGSTLLYLFPLSI-ELKEMKILFKLRGKLEPKRELSPYFENFDKYQIKCSSIN-----EN : 148
Halobacter  : DVVVTGFGSRPAIPDAVLCANLGLTLLELVTAAAA-ELADGTTLLGDESLLRALEHGPLLDALLSGLGCTARSTRGN--GQA : 153
Methanococ  : EWIVKG--CELKTPDNILILIGNLGLTLLILTSLEASQLPKCYALLLTEDDSLLRKLELQPLLDALLKQLNIEAFSSKLD--GTA : 147
Methanopyr  : EATVSGFGDSPRAPEDVLELCGNLGLTLTLLGCCLGLAA-LVEGTTLLLTLEDDSLLRSLPLVGDLLAALLRSLGVDARGRVVRGEEYP : 151
Methanosar  : NLIIQGSNGKPGIPDDVLELAANLGLTLILPMTALAG-ELTDGITLLGLTLEDSLLRTLPLNGPLEEVLWNRLCAKACSTRGN--ERA : 143
Methanosar  : NLIIHGFNGKPNVPDDVLLYLGMSGLTLLLLMTALAG-ELTDGITLLGLTLEDSLLRTLELNGPLLKTLLNQLGASACSTRGN--KKA : 143
Methanothe  : AWTVHGSGGELETPDDVLLYLGMSGLTLLILMTSLLAG-ELAEMYTLLGTCDESLLRTLLEMQPLLDALLRPLGVEALSSRMN--GLP : 144
ARoA-Ecoli  : CELIIGNGGPLHAEGALELELFLGMALTALILPLAAALC-ELGSNDILLTLEEPRLLKEPPLEIGHLVDALLRLGGAKITYLEQE--NYP : 149
Bacillus_S  : VVIHGKGIDALKEPBSLLLVGNLGLTLLMLGLLA-GRPFYSAVALEDESLLAKLPLMKRVTEPLLKKMGARIDGRAGG--EFT : 144
AROA_AGRSP  : IDGVGN--CGLLAEBAPLLDFGNAALGCELLTHGLVC-ELYDFDSTFIELDASLLTKLELMGRVLNPLREHGVQVKSEDGDR---L : 152
```

```
                         *        180         *        200         *        220         *        240
GRG-1       : ELVILQLSP-LKPADVTLDGSLSLELQLTLGLLAYAAADASDVAIKVTNLKLERPYLIDLTDLDLIKRFGLKTPENRN-Y--EELY : 217
Aeropyrum_  : LLKVSLP-LRRASVELDAALELSVLATSLLLIAGSRL-GEFELSAARLS-ELRGLLWLTDLESLSMLGVLEREGYR----LLR : 219
Archaeoglo  : LFSWQELV-IKGGEVELBAPSLE-LVCSELLFALSLABGDSSLRVEKVK-ELOPTLLLTDLDVLRESGCKLEREGN-----FEH : 212
Clostridiu  : DLQIKLGR-LKACHFNLLPGNLELSLQLISGLLELSLPFLEGDSILNNTTELELGVCLLWLLELDLHLKRFCELELENKAYK----SLF : 221
Clostridiu  : DLNNIELS-LKCCEPFKLLKCNLELSLQLISGLLEPTLPLLKDDSKLIITTELELKCLLWLLDLHLRKFLGVTLKNNNYR----ELL : 218
Fusobacter  : KLLLDLEE-LKSCVYELDGNLELSLQLISGLLELSLPLLNGNSKLLIIKCKLELSSLLVWLILTLDCLNKLGICNLLINNSYK----EPI : 223
Halobacter  : DLVVDEP-VSGGSVALPGDLESLVLATALLLMAGAVTETGIEKTDLITTELKLALPVLELTLDLLDAFLGLGASEKTAAG-----ER : 227
Methanococ  : ELIWKSGKIYGNVVKLRGDLELSLNQLVSALLLLPFNKEDTELILTSPLKSLRPVLELTLLDLLNKLGLQLDKTDN------GPL : 222
Methanopyr  : ELVVISER-PLREBVAVYGDLESLLNQLVSALLPLGAGL-GALALDVVCDLLRSLAPTVLELTVELLBRLLESVRECS-----SLB : 224
Methanosar  : ELVVPKG-IKGSRVELBSGSLESLLNQLISALLIACPLAENSTTLLSIICKLRLEAPLVLLTLELHLCLAGVGLKHTDDNNG--TRLI : 220
Methanosar  : ELVVPKG-LEGKKVSLBEGSLESLLNQLISALLIACPLAENSTTLLSIICKLKLEAPLVLLTLIELHLELAGLKLKHTDENNG--TRLI : 220
Methanothe  : ELIWREG-LRGGSTSLRGDLESLSLNQLSSLLILAAPLT-EGVELMVEGDFISLRPVLLELTLDVERLSLPDYSEG------TER : 217
ARoA-Ecoli  : PLRLQLGG-FTGCNVDLDGSLSLEGLVLATALLLMTAPLAPEDTVLRIKGDLVLSKPVLLELTNLLLKTLGGELRNQHYQ----QLV : 224
Bacillus_S  : PLSNSLEA-SLKGIDYLSPVAEANILKSAWLLLAGLQAEGTTTLLTEPHKS----R-ELHELRLLLSAPLGLLELSEDQTS-----VS : 213
AROA_AGRSP  : PLTLRLPKTPTPITYRVPMALELALVKSAWLLLAGLNTPGITTLLIEPIMTR-----ELELEKLLLQGLECANLTVETDADGVRTIR : 227
```

Fig. 2B

```
              *         260         *         280         *         300         *         320
GRG-1      : FKAGNVYDETKHQRYT.....GGA.L..GA.AG----P..RG.DIA.T.A.KA..QA.MSAN.G.AID---AK---- : 286
Aeropyrum_ : L..TP-----KPVDAA.P...S.S..U.A.CA.AG----R...KG.RPVDP.P.R.A.EL.RS...R.RVEG--GV---- : 284
Archaeoglo : IP.SQ-SFKLR--RYD.PA..S.S.S.L.A.CL.AG----E.V.KG.PE-S..C.RK..DICRE.GGS.EWDKKRGV---- : 280
Clostridiu : IK.NQ---KCKGTKYK.E...SQ.AF..S.GI.NC----N.NCKD.NIS.L..KV..D.I.KK..CA.D-----EK---- : 285
Clostridiu : IK.NQ---SYKPMNYK.E...SQ.AFYFS.CA.GS----E.NCLD.DLS.Y.C.KEC.EI.EG...R.IESQ--ER---- : 285
Fusobacter : IE.NQ---TYKSGNYQ.BA..SQVA.F.V.NS.GS----N.K.NG.NVN.L..KK..D.F.SE.DNWTK---------- : 285
Halobacter : V.RCQ-AYAPSCAKYA.P.C.S.S.L.A.GA.AAADGAA.V.KG.HP-SA.C.AA..DV.ER..G.D.DWDTESGV---- : 301
Methanococ : .Y.N---QKYKPIDYI.E...S.S.L.A.GVL.IN---SM.T.HEN.FANS.K.COKA..NI.KE.G.D.KVKK--DK---- : 290
Methanopyr : .E.RPR----SPCKLR.EN...S.A.C.F.ALCA.GG----E.R.EG.DLD.SHPR.R..EIT.RE.GRE.RRID--GG---- : 290
Methanosar : IP.KQ-KYDLK--QYT.P.D.SS.S.L.A.AA.LE--CSE.T.KN.FP-SK.C.KV.DT.KQ.C.D.TWDMEAGI---- : 290
Methanosar : IP.KQ-KYDLK--EYT.P.D.SS.S.L.A.AA.TE--CSE.T.KN.FP-SK.C.KL.IE.T.KQ.C.D.TWDREAGI---- : 290
Methanothe : V.P----AVYRGLDYT.E.C.S.S.L.AC.VAAAG---GD.L.RN.FRD.R.C.RI.D.I.SD.C.E.RRCE--DH---- : 284
AroA-Ecoli : VK.GQ-SYQSPGTYL.E.E.A.S.S.F.A.AA.KG---GT.G.TG.GENEH.C.IRFADV.RK.G.T.CWG---DD---- : 292
Bacillus_S : IA.CQ---KLTAADIF.F.E.S.AF.A.GA.VP---NS.RIV.L.KNVGLNPTRTG.ID.V.QN.G.K.EIKPSADSGAEP : 286
AROA_AGRSP : IE.RG---KLT.GQVID.P.C.P.S.TA.P.V.AL.VP----GSD.T.IE.NVL.HNPTRTG.L.LT.QE.G.D.EVINPRLACGED : 300

*         340         *         360         *         380         *         400
GRG-1      : --EIKLHPAD.NAF.E.A.ATDC.---D.F.P.VA..SYCK.E.F.KGVSR.AH.ES..GLT.QDEFC..E.VE.HLEC.L.R : 361
Aeropyrum_ : --VAVESTGP.E.P.D.V.LDGS.---D.A.VAA.L.AYAR.V.P.LRGLER.K.YES.D.SA.AWN.A.L.VEARVGGIL.E : 359
Archaeoglo : --IRAEES-E..G.R.L.ASDI.---D.V.T.A.L.AVAK.R.R.YNAXH.D.I.E.I.D..EC.HQN.KA.L.VESKPLK.GLI : 354
Clostridiu : --SFSSKKSHTHC.V..ASQC.---L.V.I.S.D.ALSE.T.K.IVNAAR.I.E.S..KA.ATE.N.GAE.VELE.CLL : 360
Clostridiu : --SLSIIHGD.NGTI.DASQC.---L.I.V.T.A.ALSKE.E.P.INGER.I.IRE.C.T.N.A.CTE.N.L.AD.KHLK.CLI : 360
Fusobacter : --------NEK.ID.GSET.---L.I.L.S..V.A.CISKK.EI.VNIAR.I.I.ES.D.SATVQE.S.L.FD.IEKE.SIL : 352
Halobacter : --ITVQRS-E..G.E.GVADT.---L.T.A..GAAAD.T.R.TDAKH.V.Y.ET..A.A.ABS.S.L.AS.EERP.E.LV : 375
Methanococ : --VIIEGEYS.KG.D.N.VKDI.---D.V.T.A.L.GCFAE.K.R.YNG.H.L.RE.C.D.RACAVE.R..GAD.EEKP.GLI : 365
Methanopyr : --IVVRSTGR.EC.E.L.SDS.---L.V.I.T.A.A..CFAE.V.R.IENVCH.T.Y.E.V.D.RA.AAKE.P.FVE.REGK.WLE : 365
Methanosar : --VTVRCGRK.KA.T.F.ACGSTE---L.V.T.A.L.SVAE.T.P.IENAXH.V.Y.ET.P.HA.PATE.P.K.P.VS.KHEM.SLT : 365
Methanosar : --VTVRCGRK.KA.T.F.ACATE---L.V.T.A.V.SVAE.T.P.IENAXH.V.Y.ET.D.P.HA.SA.ATE.P.K.V.KHEKK.SLT : 365
Methanothe : --VRIASTGE.SG.E.S.L.LHDA.---L.L.T.A.L.GALAT.R.E.IGCGVKHA.P.Y.ET.D.L.STCAAE.R.L.VD.T.LP.CHI : 359
AroA-Ecoli : --YISCTRGE.NA.D.D.MNHI.---L.A.H.T.A.A..LFAKE.T.P.RNIYNW.V.E.T.P.F.A.A.A.E.R.V.CAE.EECH.YIR : 367
Bacillus_S : YGDLIIETSS.KA.E.GCDII.RLI.E.I.V.A.L.L.TQAE.E.T.V.IKDAAE.L.NV.E.T.P.D.T.VSE.R.L.AE.EPTA.CHK : 366
AROA_AGRSP : VADLRVRSST.KG.T.PED RA.SMI.EY.I.A.A.L.AFAE.E.A.V.NGLEE.L.V.ES.D.L.SA.ANG.KLN.V.DCDEGETS.LV : 380

*         420         *         440         *         460         *
GRG-1      : .I.GK-----GVKGAE.SS.RH.HI.A.L.ACA.AALKAVGETT.EHAEA.WK.I.D.YSD.KQ.L.GV.SLNHQPNPS- : 431
Aeropyrum_ : I.R.G-------GVEGCVARS.WG.HPIA.ARA.AGLGARRPVA.EGFSR.S.PD..T.GF.EB.D.AR.L.AR.EAVKGCGV-- : 427
Archaeoglo : IK.GK------GEFRGVI.DS.FG.HPIALAFS.LGL.GE--VKCRNAE.V.SVS.F.G.P.RVE.KQ.L.GD.HEWSLGE--- : 416
Clostridiu : IE.KE---KLKGGE---E.SUN.HR.A.IALAL.C.A.AR.RCEESVT.NGSE.C.SKE.S.F.C..F.EDFKSL.G.CI.REH------- : 428
Clostridiu : IN.VK---DLICGE----.Y.SHK.HPIA.S.LA.ASTRCKKEVI.KEPDC.KK.E.I.C.F.ED.FKSL.G.CI..REH------- : 424
Fusobacter : IN.SRKNPNEISNNSPIS.S.SHS.HP.IA.TVA.ASTCYEG.RI..DNLDC..KKS.I.NF.WKVPLSL.C.KH.YEYLC----- : 424
Halobacter : .R.GDT-----ELSGAS.D.CRG.HRL.V.L.A.A.AGLVADCETT.ACSEH.D.V.E.F.D.F.EV.AGL.AD.TDG--------- : 439
Methanococ : IR.VK------KLKGAB.N.YH.HPLVAFT.AGLKAEGETI.EGREA.KI.E.F.NE.V.DV.KSD.AN.EVK------- : 429
Methanopyr : IV.G--------EPVGAR.D.S.RG.HP.A.LA.A.VGFARGKTV.ERADA.A.SI.S.T.R.F.WED.ASW.V.P.HSV----- : 428
Methanosar : IT.C--------TLE.GAE.HC.WD.HRI.V.L.S.LA.AGMVAC--NTI.DTTES.S.I.S.T.DF.FKD.RNL.CA.K.KEIPEE---- : 430
Methanosar : IT.C--------ELKGAE.HC.WD.HPIV.L.S.LA.AGMVAC--NTI.DTTES.A.I.S.T.DF.FED.SNL.CVK.I.KQISEE---- : 430
Methanothe : IE.G---------ASGGT.L.S.HG.HP.LA.I.AFT.I.GLREG--IT.I.RDAEVF.SV.E.F.D.F.PER.L.MQI.CC.R.NLS------- : 419
AroA-Ecoli : .T.PPE------KLNFAE.L.A.YM.HH.A.L.C.FS.L.VALSDT-PVT.L.DPKCTARTF.ED.T.F.EQ.L.AR.ISQAA---------- : 427
Bacillus_S : W.E.KQT-----LKGGAA.L.SS.HG.HP.IG.T.HL.CI.A.SCIT.EP.IE.EHTDA.HV.F.T.T.F.EH.NKH.SKKS---------- : 428
AROA_AGRSP : H.E.RPDGKGLGNASGGAA.A.HL.HH.A.I.SFL.MGLVSENPVT.DDATM.AT.SE.E.E.MD.L.AGL.CAK.ELSDTKAA-- : 455
```

Fig. 3A

```
                          *         20         *         40         *
GRG1          : -------------------------------------------------- :   -
Z. mays       : -------------------------------------------------- :   -
Arabidopsis   : MASSLTSKSILGCTKPASSSFLPSELRRLSSPAVQISLHSQTRKNFRQSW   :  50
E. coli       : -------------------------------------------------- :   -
Agrobacterium : -------------------------------------------------- :   -
Sacchromyces  : -------------------------------------------------- :   -

60         *         80         *        100
GRG1          : ---------------------MKVTIQPGDLTG----ILQS           :  16
Z. mays       : ---------------------AGAEEIVLQPIKEISG----TVKL       :  20
Arabidopsis   : GLKKSDLMLNGSEIRPVKVRASVSTAEKASEIVLQPIREISG----LIKL  :  96
E. coli       : ---------------------------MESLTLQPIARVDG----TINL  :  18
Agrobacterium : ---------------------MSHGASSRPATARKSSGLSG----TVRI  :  24
Sacchromyces  : ---------------------RFILTDETLVYEFKDIPADQQKVVIP    :  26

*         120        *         140        *
GRG1          : PASKSSMQRACAAELVAKGISEIINPGHSNDDKAARDIVSRLG---ARLE :  63
Z. mays       : PSSKSLSNRILLLAALSEGTIVVDNLLNSEDVHYMLGALRTLG-LSVEAD :  69
Arabidopsis   : PGSKSLSNRILLLAALSEGTIVVDNLLNSDDINYMLDALKILG-LNVETH : 145
E. coli       : PGSKSVSNRALLLAALAHGKTVLTNLLDSDDVRHMLNALTALG-VSYTLS :  67
Agrobacterium : PGDKSISHRSFMFGGLASGETRITGLLEGEDVINTGKAMQAMG-ARIRKE :  73
Sacchromyces  : PGSKSLSNRALLLAALGEGQCKIKNLLHSDDTKHMLTAVHELKGATLSWE :  76

160        *         180        *        200
GRG1          : DQPDGSLQITSEGVKPV------APFIDCGESGLSIRMFTPIVALSKE-- : 105
Z. mays       : KAAKRAVVVGCGGKFPV-EDAKEEVQLFLGNAGTAMRPLTAAVTAAGGNA : 118
Arabidopsis   : SENNRAVVEGCGGVFPASIDSKSDIELYLGNAGTAMRPLTAAVTAAGGNA : 195
E. coli       : ADRTRCEIIGNGGPLHA----EGALELFLGNAGTAMRPLAAALCLGSN-- : 111
Agrobacterium : GDTWIIDGVGNGGLLAP------EAPLDFGNAATGCRLTMGLVGVYDFDS : 117
Sacchromyces  : DNGETVVVEGHGGSTLS----ACADPLYLGNAGTASRFLTSLAALVNSTS : 122

*         220        *         240        *
GRG1          : ---EVTIKGSGSLVTRPMDFFDEILPHLGVKVKSNQGK-LPLVIQG-P   : 148
Z. mays       : ---TYVLDGVPRMRERPIGDLVVGLKQLGADVDCFLGTDCPPVRVNGIGG : 165
Arabidopsis   : ---SYVLDGVPRMRERPIGDLVVGLKQLGADVECTLGTNCPPVRVNANGG : 242
E. coli       : ---DIVLTGEPRMKERPIGHLVDALRLGGAKITYLEQENYPPLRLQG-G  : 156
Agrobacterium : ---TFIG-DASLTKRPMGRVLNPLREMGVQVKSEDGDR-LPVTLRG-P   : 159
Sacchromyces  : SQKYIVLTGNARMQQRPIAPLVDSLRANGTKIEYLNNEGSLPIKVYTDSV : 172

260        *         280        *        300
GRG1          : LKPADVTVDGSLGSQFLTGLLAYAAADASDVAIKVT-NLKSRPYIDLTL  : 197
Z. mays       : LPGGKVKLSGSISSQYLSALLMAAPLALGDVETEILD-KLISIPYVEMTL : 214
Arabidopsis   : LPGGKVKLSGSISSQYLTAILMAAPLALGDVETEIVD-KLISVPYVEMTL : 291
E. coli       : FTGGNVDVDGSVSSQFLTALLMTAPLAPEDTVIRIKG-DLVSKPYIDITL : 205
Agrobacterium : KTPTPITYRVPMASAQVKSAVLLAGLNTPGITTVIEP-----IMTRDHTE : 204
Sacchromyces  : FKGGRIELAATVSSQYVSSILMCAPYAEEPVTLALVGGKPISKLYVDMTI : 222
```

Fig. 3B

```
                          *         320         *         340         *
GRG1          : DVMKRFGLKTPENRNYEEFYFKAGNVIDETKMQRYTVEGDWSGGAFLLVA  : 247
Z. mays       : RLMERFGVKAEHSDSWDRFYIKGGQKYKSP--KNAYVEGDASSASYFLAG  : 262
Arabidopsis   : KLMERFGVSAEHSESWDRFFVKGGQKYKSP--GNAYVEGDASSASYFLAG  : 339
E. coli       : NLMKTFGVEIEN-QHLQQFVVKGGQSYQSP--GTYLVEGDASSASYFLAA  : 252
Agrobacterium : KMLQGFGANLTVETDADGVRTIRLEGRGKLTGQVIDVPGDPSSTAFPLVA  : 254
Sacchromyces  : KMMEKFGINVETSTTEPYTYYIPKGHYINP--SEYVIESDASSATYPLAF  : 270

*         360         *         380         *         400
GRG1          : GAIAG--PITVRGLDIASTCADKAIV-QALMSANAGIAIDAKEIKLH-P-  : 292
Z. mays       : AAITGG-TVIVEGCGTTSLCGDVKFA-EVLEMMGAKVTWTETSVTVTGPP  : 310
Arabidopsis   : AAITGE-TVIVEGCGTTSLCGDVKFA-EVLEKMGCKVSWTENSVTVTGPS  : 387
E. coli       : AAIKGG-TVKVTGIGRNSMCGDIRFA-DVLEKMGATICWGDDYISCI---  : 297
Agrobacterium : ALLVPGSDVILNVLMNPTRTGLILT---LQEMGADIEVINPRLAGGEDV  : 301
Sacchromyces  : AAMTGT-TVIVPNIGFESLCGDARFARDVLKPMGCKITQTATSTTVSGPP  : 319

*         420         *         440         *
GRG1          : ---------ADLNAFEFDATDCPDLFPPLVALASYCKG-------ETKI  : 325
Z. mays       : REP----FGRKHLKAIDVNMNKMPDVAMTLAVVALFADG-------PTAI  : 349
Arabidopsis   : RDA----FGMRHLRAIDVNMNKMPDVAMTLAVVALFADG-------PTTI  : 426
E. coli       : --------RGELNAIDMDMNHIPDAAMTLATAALFAKG-------TTTL  : 331
Agrobacterium : ADLRVRSSTLKGVTVPEDRAPSMIDEYPILAVAAAFAEG-------ATVM  : 344
Sacchromyces  : --------VGTLKPLKHVEMEPYTDAFLTACVVAAISHDSDPNSANTTTI  : 361

*         460         *         480         *         500
GRG1          : KGVSRLAHKESDRGLTLQDEFGKMGVEIHLEGDLMRVIG----------G  : 365
Z. mays       : RDVASWRVKETERMVAIRTELTKLGASVEEGPDYCIIT----------PP  : 389
Arabidopsis   : RDVASWRVKETERMIAICTELRKLGATVEEGSDYCVIT----------PP  : 466
E. coli       : RNIYNWRVKETDRLFAMATELRKVGAEVEDGHDYIRIT----------PP  : 371
Agrobacterium : NGLEELRVKESDRLSAVANGLKLNGVDCDEGETSLVVRG----RPDGKGL  : 390
Sacchromyces  : EGLANQRVKECNRLLAMATELAKFGVKTTELPDGIQVHGLNSIKDLKVPS  : 411

*         520         *         540         *
GRG1          : KGVKGAEVSSRHDHRIAMCAVAALKAVG---------ETTIEHAEAVNK  : 406
Z. mays       : EKINVTAIDTYDDHRMAMAFSLAACAE---------VPVIIRDPGCTRK  : 429
Arabidopsis   : KKVKPAEIDTYDDHRMAMAFSLAACAD---------VPITINDPGCTRK  : 506
E. coli       : EKINFAEIATYNDHRMAMCFSLVALSD---------TPVIILDPKCTAK  : 411
Agrobacterium : GNASGAAVATHLDHRIAMSELVMGLVSE--------NPVIVDDATMIAT  : 431
Sacchromyces  : DSSGPVGVCTYDDHRVAMSFSLLAGMVNSQNERDEVANPVRILERHCTGK  : 461

*         560         *         580         *
GRG1          : SYPDFYSDLKQLGGVVSLNHQFNFS-------------------  : 431
Z. mays       : TFPDYFDVLSTFVKN----------------------------  : 444
Arabidopsis   : TFPDYFQVLERITKH----------------------------  : 521
E. coli       : TFPDYFEQLARISQAA---------------------------  : 427
Agrobacterium : SFPEFMDLMAGLGAKIELSDTKAA-------------------  : 455
Sacchromyces  : TWPGWNDVLHSELGAKLDGAEPLECTSKKNSKKSVVIIGMRAAGE  : 506
```

GENES CONFERRING HERBICIDE RESISTANCE

CROSS REFERENCE TO RELATED APPLICATION

This application is a divisional of U.S. application Ser. No. 10/739,610, filed Dec. 18, 2003, which claims the benefit of U.S. Provisional Application Ser. No. 60/434,789, filed Dec. 18, 2002, the contents of which are hereby incorporated in their entirety by reference herein.

FIELD OF THE INVENTION

This invention provides novel genes encoding herbicide resistance, which are useful in plant biology, crop breeding, and plant cell culture.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phosphoshikimic acid to 5-enolpyruvyl-3-phosphoshikimic acid. Inhibition of this enzyme (5-enolpyruvylshikimate-3-phosphate synthase; referred to herein as "EPSP synthase") kills plant cells by shutting down the shikimate pathway, thereby inhibiting aromatic acid biosynthesis.

Since glyphosate-class herbicides inhibit aromatic amino acid biosynthesis, they not only kill plant cells, but are also toxic to bacterial cells. Glyphosate inhibits many bacterial EPSP synthases, and thus is toxic to these bacteria. However, certain bacterial EPSP synthases have high tolerances to glyphosate. Several such bacterial EPSP synthase have been previously isolated. Analysis of the existing sequences of glyphosate resistant and sensitive EPSP synthases does not predict a priori whether a given EPSP synthase is glyphosate resistant or glyphosate sensitive, or the level of resistance of any amino acid sequence to glyphosate inhibition. Furthermore, the sequences of known EPSP synthases do not predict all sequences capable of functioning to encode EPSP synthase activity, nor the level of resistance to glyphosate of that amino acid sequence.

Plant cells resistant to glyphosate toxicity can be produced by transforming plant cells to express glyphosate-resistant bacterial EPSP synthases. Notably, the bacterial gene from *Agrobacterium tumefaciens* strain CP4 has been used to confer herbicide resistance on plant cells following expression in plants. A mutated EPSP synthase from *Salmonella typhimurium* strain CT7 confers glyphosate resistance in bacterial cells, and confers glyphosate resistance on plant cells (U.S. Pat. Nos. 4,535,060; 4,769,061; and 5,094,945). However, there is a need for other herbicide resistance genes.

SUMMARY OF INVENTION

Compositions and methods for conferring herbicide resistance to plants, plant cells, tissues and seeds are provided. Compositions comprising a coding sequence for a polypeptide that confers resistance or tolerance to glyphosate herbicides are provided. The coding sequences can be used in DNA constructs or expression cassettes for transformation and expression in plants and other organisms. Compositions also comprise transformed bacteria, plants, plant cells, tissues, and seeds.

In particular, isolated nucleic acid molecules corresponding to glyphosate resistant nucleic acid sequences are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:2 or the nucleotide sequence set forth in SEQ ID NO:1 and mutants and variants thereof.

DESCRIPTION OF FIGURES

FIGS. 2A and 2B show an alignment of GRG-1 protein (SEQ ID NO:2) to related proteins from *Aeropyrum pernix* (SEQ ID NO:3), *Archaeoglobus fulgidus* (SEQ ID NO:4), *Clostridium acetobutylicum* (SEQ ID NO:5), *Clostridium perfringens* (SEQ ID NO:6), *Fusobacterium nucleatum* (SEQ ID NO:7), *Halobacterium* sp. NRC-1 (SEQ ID NO:8), *Methanococcus jannushii* (SEQ ID NO:9), *Methanopyrus kandleri* (SEQ ID NO:10), *Methanosarcina mazei* (SEQ ID NO:11), *Methanosarcina acetivorans* (SEQ ID NO:12), *Methanothermobacter thermautotrophicus* (SEQ ID NO:13), *Escherichia coli* (SEQ ID NO:14), *Bacillus subtilis* (SEQ ID NO:15), and *Agrobacterium* sp. CP4 (SEQ ID NO:16).

FIGS. 3A and 3B show an alignment of the GRG-1 protein (SEQ ID NO:2) to related proteins from *Zea mays* (SEQ ID NO:17), *Arabidopsis thaliana* (SEQ ID NO:18), *Escherichia coli* (SEQ ID NO:14), *Agrobacterium* sp. CP4 (SEQ ID NO:16), and *Saccharomyces cerevisiae* (SEQ ID NO:19).

DETAILED DESCRIPTION

Figure 1:
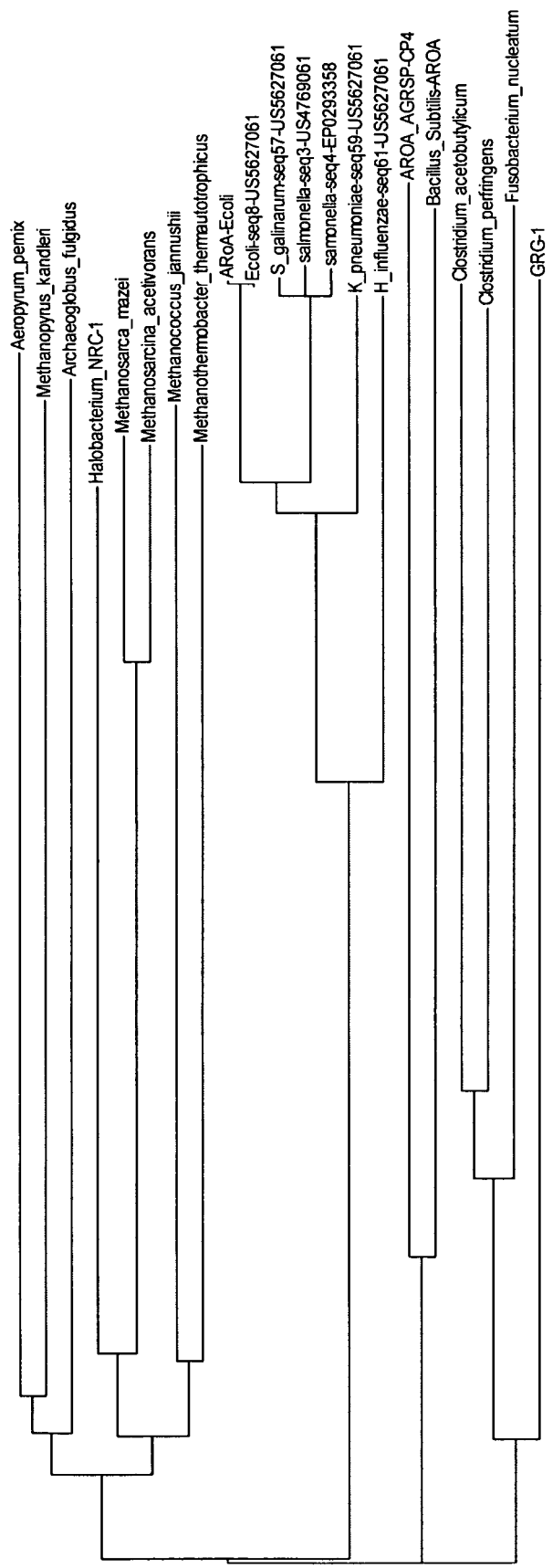
FIG. 1 shows an alignment of GRG-1 protein (SEQ ID NO:2) to related proteins.

The present invention is drawn to compositions and methods for regulating herbicide resistance in organisms, particularly in plants or plant cells. The methods involve transforming organisms with nucleotide sequences encoding the glyphosate resistance gene of the invention. In particular, the nucleotide sequences of the invention are useful for preparing plants that show increased tolerance to the herbicide glyphosate. Thus, transformed plants, plant cells, plant tissues and seeds are provided. Compositions of the invention comprise nucleic acids and proteins relating to glyphosate tolerance in plants. More particularly, nucleotide sequences of the glyphosate resistance gene (GRG) and the amino acid sequences of the proteins encoded thereby are disclosed. The sequences find use in the construction of expression vectors for subsequent transformation into plants of interest, as probes for the isolation of other glyphosate resistance genes, as selectable markers, and the like.

Definitions

"Glyphosate" includes any herbicidal form of N-phosphonomethylglycine (including any salt thereof) and other forms which result in the production of the glyphosate anion in planta. "Glyphosate resistance gene" or "GRG" or "glyphosate resistance encoding nucleic acid sequence" includes a DNA segment that encodes all or part of a glyphosate resistance protein. This includes DNA segments that are capable of expressing a glyphosate resistance protein in a cell, such as a gene.

A "glyphosate resistance protein" includes a protein that confers upon a cell the ability to tolerate a higher concentration of glyphosate than cells that do not express this protein, or to tolerate a certain concentration of glyphosate for a longer time than cells that do not express this protein. This ability to survive in the presence of glyphosate is due to the protein having "glyphosate resistance activity." By "tolerate"

is intended to survive, or to carry out essential cellular functions such as protein synthesis and respiration.

"Plant cell" includes all known forms of a plant, including undifferentiated tissue (e.g. callus), suspension culture cells, protoplasts, leaf cells, root cells, phloem cells, plant seeds, pollen, propagules, embryos and the like. "Plant expression cassette" includes DNA constructs that are capable of resulting in the expression of a protein from an open reading frame in a plant cell. Typically these contain a promoter and a gene. Often, such constructs will also contain a 3' untranslated region. It is understood that if a construct does not per se contain a 3' transcription termination signal, that transcription will be terminated nonetheless, via recognition by the transcription apparatus of the most closely located acceptable sequence. Often, such constructs may contain a 'signal sequence' or 'leader sequence' to facilitate co-translational or post-translational transport of the peptide to certain intracellular structures such as the chloroplast (or other plastid), endoplasmic reticulum, or Golgi apparatus.

"Signal sequence" includes sequences that are known or suspected to result in cotranslational or post-translational peptide transport across the cell membrane. In eukaryotes, this typically involves secretion into the Golgi apparatus, with some resulting glycosylation. "Leader Sequence" includes any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

"Plant transformation vector" includes DNA molecules that are necessary for efficient transformation of a plant cell. Such a molecule may consist of one or more plant expression cassettes, and may be organized into more than one 'vector' DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451).

"Vector" refers to a nucleic acid construct designed for transfer between different host cells. "Expression vector" refers to a vector that has the ability to incorporate, integrate and express heterologous DNA sequences or fragments in a foreign cell.

"Transgenic plants" or "transformed plants" or "stably transformed plants or cells or tissues" refers to plants that have incorporated or integrated exogenous nucleic acid sequences or DNA fragments that are not present in the i.e. "untransformed" plant or plant cell.

"Heterologous" generally refers to the nucleic acid sequences that are not endogenous to the cell or part of the native genome in which they are present, and have been added to the cell by infection, transfection, microinjection, electroporation, microprojection, or the like.

"Promoter" refers to a nucleic acid sequence that functions to direct transcription of a downstream gene. The promoter together with other transcriptional and translational regulatory nucleic acid sequences (also termed as "control sequences") are necessary for the expression of a gene of interest.

Provided herein is a novel gene that confers resistance to glyphosate. Further provided is the DNA sequence of this gene. Also provided is the amino acid sequence of the GRG-1 protein. The protein resulting from translation of this gene allows cells to function in the presence of concentrations of glyphosate that are otherwise toxic to cells including plant cells and bacterial cells.

Preferred glyphosate resistance proteins of the present invention have an amino acid sequence sufficiently identical to the amino acid sequence of SEQ ID NO:2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have at least about 45%, about 55%, or about 65% identity, preferably about 75% identity, more preferably about 85%, most preferably about 90%, about 91%, about 92%, about 93%, about 94%, about 95%, about 96%, about 97%, about 98%, or about 99% identity.

Sequences that are sufficiently identical will have a common functional activity and may have one or more common structural domains or motifs, such as those shown in FIGS. 3A, B and C. Functional activity of herbicide resistance proteins may be determined by methods known in the art. See, for example, Osuna et al. (2001) *Pest Manag. Sci.* 59:1210-1216; Ye etal. (2001) *Plant J.* 25:261-270.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to GRG-like nucleic acid molecules of the invention. BLAST protein searches can be performed with the BLASTX program, score=50, wordlength=3, to obtain amino acid sequences homologous to glyphosate resistance protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www.ncbi.nlm.nih.gov. Another preferred, non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the vector NTi Program Suite (Informax, Inc). After alignment of amino acid sequences with ClustalW, the percent amino acid identity can be assessed. A non-limiting example of a software program useful for analysis of ClustalW alignments is Gene-Doc™. Genedoc™ (Karl Nicholas) allows assessment of amino acid (or DNA) similarity and identify between multiple proteins. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3 ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated glyphosate resistance encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A glyphosate resistant protein that is substantially free of cellular material includes preparations of protein having less than about 30%, 20%, 10%, or 5% (by dry weight) of non-glyphosate resistant protein (also referred to herein as a "contaminating protein"). Various aspects of the invention are described in further detail in the following subsections.

Isolated Nucleic Acid Molecules

One aspect of the invention pertains to isolated nucleic acid molecules comprising nucleotide sequences encoding glyphosate resistance proteins and polypeptides or biologically active portions thereof, as well as nucleic acid molecules sufficient for use as hybridization probes to identify glyphosate resistance encoding nucleic acids. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the proteins of the present invention include sequences set forth in SEQ ID NO:1 and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the glyphosate resistance protein encoded by these nucleotide sequences is set forth in SEQ ID NO:2. The invention also encompasses nucleic acid molecules comprising nucleotide sequences encoding partial-length glyphosate resistance proteins, including the sequence set forth in SEQ ID NO:1, and complements thereof.

Nucleic acid molecules that are fragments of these glyphosate resistance-encoding nucleotide sequences are also encompassed by the present invention. By "fragment" is intended a portion of the nucleotide sequence encoding a glyphosate resistance protein. A fragment of a nucleotide sequence may encode a biologically active portion of a glyphosate resistance protein, or it may be a fragment that can be used as a hybridization probe or PCR primer using methods disclosed below. Nucleic acid molecules that are fragments of a glyphosate resistance nucleotide sequence comprise at least about 15, 20, 50, 75, 100, 200, 300, 350, 400,450,500, 550, 600, 650, 700, 750, 800, 850, 900, 950, 1000, 1050, 1100, 1150, 1200, 1250 nucleotides, or up to the number of nucleotides present in a full-length glyphosate resistance encoding nucleotide sequence disclosed herein (for example, 1293 nucleotides for SEQ ID NO:1) depending upon the intended use.

A fragment of a glyphosate resistance encoding nucleotide sequence that encodes a biologically active portion of a protein of the invention will encode at least about 15, 25, 30, 50, 75, 100, 125, 150, 175, 200, 250, 300, 350, or 400 contiguous amino acids, or up to the total number of amino acids present in a full-length glyphosate resistance protein of the invention (for example, 432 amino acids for the protein of the invention).

The invention also encompasses variant nucleic acid molecules. "Variants" of the glyphosate resistance encoding nucleotide sequences include those sequences that encode the glyphosate resistance proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the glyphosate resistance proteins disclosed in the present invention as discussed below. Generally, nucleotide sequence variants of the invention will have at least about 45%, 55%, 65%, 75%, 85%, 90%, 91%, 92%, 93%, 94%, 95%, 96%, 97%, 98%, or 99% identity to a particular nucleotide sequence disclosed herein. A variant nucleotide sequence will encode a glyphosate resistance protein that has an amino acid sequence having at least about 45%, 55%, 65%, 75%, 85%, 90%, 91%, 92%, 93%, 94%, 95%, 96%, 97%, 98%, or 99% identity to the amino acid sequence of a glyphosate resistance protein disclosed herein. These variants will also retain functional activity, as determined by methods known in the art, such as these described in Example 8.

The skilled artisan will further appreciate that changes can be introduced by mutation into the nucleotide sequences of the invention thereby leading to changes in the amino acid sequence of the encoded glyphosate resistance proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a glyphosate resistance protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions, such as those shown in FIGS. 3A, B, and C, that retain function. In general, such substitutions would not be made for conserved amino acid residues, or for amino acid residues residing within a conserved motif, such as the residues shown in Table 6 where such residues are essential for protein activity. However, one of skill in the art would understand that functional variants may have minor conserved or nonconserved alterations in the conserved domains.

Alternatively, variant nucleotide sequences can be made by introducing mutations randomly along all or part of the coding sequence, such as by saturation mutagenesis, and the resultant mutants can be screened for ability to confer glyphosate resistance activity to identify mutants that retain activity. Following mutagenesis, the encoded protein can be expressed recombinantly, and the activity of the protein can be determined using standard assay techniques.

Using methods such as PCR, hybridization, and the like corresponding glyphosate resistance sequences can be identified, such sequences having substantial identity to the sequences of the invention. See, for example, Sambrook J., and Russell, D. W. (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the glyphosate resistance nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known glyphosate resistance-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of glyphosate resistance-encoding nucleotide sequence of the invention or a fragment or variant thereof. Preparation of probes for hybridization is generally known in the art and is disclosed in Sambrook and Russell, 2001, supra, herein incorporated by reference.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the GRG sequence of the invention. Methods for preparation of probes for hybridization and for construction of cDNA and genomic libraries are generally known in the art and are disclosed in Sambrook et al. (1989) *Molecular Cloning. A Laboratory Manual* (2d ed., Cold Spring Harbor Laboratory Press, Plainview, N.Y.).

For example, the entire GRG sequence disclosed herein, or one or more portions thereof, may be used as a probe capable of specifically hybridizing to corresponding GRG-like sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify corresponding GRG sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al., 1989, supra).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCi, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) Anal. Biochem. 138:267-284: $T_m=81.5°$ C.+16.6 (log M)+0.41 (% GC)−0.61 (% form) −500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al., 1989, supra.

Isolated Proteins

Glyphosate resistance proteins are also encompassed within the present invention. By "glyphosate resistance protein" or "glyphosate tolerant protein" is intended a protein having the amino acid sequence set forth in SEQ ID NO:2, as well as fragments, biologically active portions, and variants thereof.

"Fragments" or "biologically active portions" include polypeptide fragments comprising amino acid sequences sufficiently identical to the amino acid sequence set forth in SEQ ID NO:2 and that exhibit glyphosate resistance activity. A biologically active portion of a glyphosate resistance protein can be a polypeptide which is, for example, 10, 25, 50, 100 or more amino acids in length. Such biologically active portions can be prepared by recombinant techniques and evaluated for glyphosate resistance activity. As used here, a fragment comprises at least about 8 contiguous amino acids of SEQ ID NO:2. The invention encompasses other fragments, however, such as any fragment in the protein greater than about 10, 20, 30, 50, 100, 150, 200, 250, and 300 amino acids.

By "variants" is intended proteins or polypeptides having an amino acid sequence that is at least about 45%, 55%, 65%, preferably about 75%, about 85%, most preferably about 90%, about 91%, about 92%, about 93%, about 94%, about 95%, about 96%, about 97%, about 98%, or about 99% identical to the amino acid sequence of SEQ ID NO:2, and that retain glyphosate resistance activity. Variants also include polypeptides encoded by a nucleic acid molecule that hybridizes to the nucleic acid molecule of SEQ ID NO:1, or a complement thereof, under stringent conditions. Variants include polypeptides that differ in amino acid sequence due to mutagenesis.

GRG-1 is Useful as a Transformation Reporter and Selectable Marker

In one aspect of the invention, the GRG-1 gene is useful as a marker to assess transformation of bacterial or plant cells. Transformation of bacterial cells is accomplished by one of several techniques known in the art, not limited to electroporation, or chemical transformation (See for example Ausubel (ed.), Current Protocols in Molecular Biology, John Wiley and Sons, Inc. (1994)). Markers conferring resistance to toxic substances are useful in identifying transformed cells (having taken up and expressed the test DNA) from non-transformed cells (those not containing or not expressing the test DNA). By engineering GRG-1 to be (1) expressed from a bacterial promoter known to stimulate transcription in the organism to be tested, (2) properly translated to generate an intact GRG-1 peptide, and (3) placing the cells in an otherwise toxic concentration of glyphosate, one can identify cells that have been transformed with DNA by virtue of their resistance to glyphosate.

GRG-1 is Useful as a Selectable Marker/Reporter for Plant Transformation

Transformation of plant cells can be accomplished in similar fashion. First, one engineers the GRG-1 gene in a way that allows its expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this 'plant expression cassette' will be inserted into a 'plant transformation vector'. This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as 'binary vectors'. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a 'gene of interest' (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium,* and transfer of DNA by cleavage at border sequences and vir-mediated DNA transfer, as in understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethelene glycol, etc. Many types of vectors can be used to transform plant cells for achieving glyphosate resistance.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene and in this case "glyphosate") to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (e.g. "glyphosate"). The shoots are then transferred to a selective rooting medium for recovering rooted shoots or plantlets. The transgenic plantlets then grow into mature plants and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plantlets are found in Ayres and Park, 1994 (*Critical Reviews in Plant Science* 13:219-239) and Bommineni and Jauhar, 1997 (*Maydica* 42:107-120). Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Generation of transgenic plants may be performed by one of several methods, including but not limited to introduction of heterologous DNA by *Agrobacterium* into plant cells (*Agrobacterium*-mediated transformation), bombardment of plant cells with heterologous foreign DNA adhered to particles (particle bombardment), and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055; U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. No. 5,240,855; U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods,* ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues,* ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Following integration of heterologous foreign DNA into plant cells, one then applies a maximum threshold level of glyphosate in the medium to kill the untransformed cells and separate and proliferate the putatively transformed cells that survive from this selection treatment by transferring regularly to a fresh medium. By continuous passage and challenge with glyphosate, one identifies and proliferates the cells that are transformed with the plasmid vector. Then molecular and biochemical methods will be used for confirming the presence of the integrated heterologous gene of interest in the genome of transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

The present invention may be used for transformation of any plant species, including, but not limited to, monocots and dicots. Examples of plants of interest include, but are not limited to, rice, corn, alfalfa, sunflower, *Brassica* sp., soybean, cotton, safflower, peanut, sorghum, wheat, millet, and tobacco. Preferably, plants of the present invention are crop plants.

The GRG sequences of the invention may be provided in expression cassettes for expression in the plant of interest. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the GRG sequence to be under the transcriptional regulation of the regulatory regions.

The expression cassette will include in the 5'-3' direction of transcription, a transcriptional and translational initiation region (i.e., a promoter), a DNA sequence of the invention, and a transcriptional and translational termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481. Other transit peptides include the transit peptides described in U.S. Application No. 20020073443 and U.S. Application No. 20020178467. In other embodiments, the nucleic acids of interest may be targeted to the outside of the cell or to other intracellular components, such as the nucleus, mitochondrion, or endoplasmic reticulum.

Chloroplast targeting sequences are known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6):789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36):27447-27457); and the light harvesting chlorophyll a/b binding protein (LHBP) (Lamppa et al. (1988) *J. Biol. Chem.* 263:14996-14999). See also Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad Sci. USA* 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR Analysis: PCR analysis is a rapid method to screen transformed cells, tissue or shoots for the presence of incorporated gene at the earlier stage before transplanting into the soil (Sambrook and Russell, 2001, supra) PCR is carried out using oligonucleotide primers specific to the gene of interest or *Agrobacterium* vector background, etc.

Southern Analysis: Plant transformation is confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane The membrane or "blot" then is probed with, for example, radiolabeled $^{32}$P target DNA fragment to confirm the integration of introduced gene in the plant genome according to standard techniques (Sambrook and Russell, 2001, supra).

Northern Analysis: RNA is isolated from specific tissues of transformant, fractionated in a formaldehyde agarose gel, blotted onto a nylon filter according to standard procedures that are routinely used in the art (Sambrook and Russell, 2001, supra) Expression of RNA encoded by the GRG is then tested by hybridizing the filter to a radioactive probe derived from a GRG, by methods known in the art (Sambrook and Russell, 2001, supra).

Western blot and Biochemical assays: Western blot and biochemical assays and the like may be carried out on the transgenic plants to confirm the determine the presence of protein encoded by the Glyphosate resistance gene by standard procedures (Sambrook and Russell, 2001, supra) using antibodies that bind to one or more epitopes present on the glyphosate resistance protein.

GRG-1 may be Useful to Provide Herbicide Resistance to Plants

In another aspect of the invention, one may generate transgenic plants expressing GRG-1 that are more resistant to high concentrations of glyphosate than non-transformed plants. Methods described above by way of example may be utilized to generate transgenic plants, but the manner in which the transgenic plant cells are generated is not critical to this invention. Methods known or described in the art such as Agrobacterium-mediated transformation, biolistic transformation, and non-particle-mediated methods may be used at the discretion of the experimenter. Plants expressing GRG-1 may be isolated by common methods described in the art, for example by transformation of callus, selection of transformed callus, and regeneration of fertile plants from such transgenic callus. In such process, GRG-1 may be used as selectable marker. Alternatively, one may use any gene as a selectable marker so long as its expression in plant cells confers ability to identify or select for transformed cells. Genes known to function effectively as selectable markers in plant transformation are well known in the art.

Fertile plants expressing GRG-1 may be tested for the ability to resist challenge with varying concentrations of glyphosate or similar herbicides, and the plants showing best resistance selected for further breeding.

GRG-1 may be used as a Template to Generate Altered or Improved Variants

It is recognized that DNA sequence of GRG-1 may be altered by various methods, and that these alterations may result in DNA sequences encoding proteins with amino acid sequences different that that encoded by GRG-1. This protein may be altered in various ways including amino acid substitutions, deletions, truncations, and insertions. Methods for such manipulations are generally known in the art. For example, amino acid sequence variants of the GRG-1 protein can be prepared by mutations in the DNA. This may also be accomplished by one of several forms of mutagenesis and/or in directed evolution. In some aspects, the changes encoded in the amino acid sequence will not substantially affect function of the protein. Such variants will possess the desired herbicide resistance activity. However, it is understood that the ability of GRG-1 to confer glyphosate resistance may be improved by use of such techniques upon the compositions of this invention. For example, one may express GRG-1 in host cells that exhibit high rates of base misincorporation during DNA replication, such as XL-1 Red (Stratagene). After propagation in such strains, one can isolate the GRG-1 DNA (for example by preparing plasmid DNA, or by amplifying by PCR and cloning the resulting PCR fragment into a vector), culture the GRG-1 mutations in a non-mutagenic strain, and identify mutated GRG-1 genes with improved resistance to glyphosate, for example by growing cells in increasing concentrations of glyphosate and testing for clones that confer ability to tolerate increased concentrations of glyphosate.

Bacterial genes, such as the GRG-1 gene of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants of GRG-1 (SEQ ID NO:2) that encode pesticidal activity. Thus, the altered variants arising from the use of such start codons are contained in this invention. Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of gram-negative bacteria, or the endoplasmic reticulum of eukaryotic cells, the latter of which often results in glycosylation of the protein.

The following examples are offered by way of illustration and not by way of limitation.

EXPERIMENTAL

Example 1

Isolation of Strains Resistant to Glyphosate

Glyphosate-resistant bacteria were isolated by plating samples of soil on Enriched Minimal Media (EMM) containing glyphosate as the sole source of phosphorus (EMM+G). Since EMM+G contains no aromatic amino acids, a strain must be resistant to glyphosate in order to grow on this media.

Enriched Minimal Media (EMM), per Liter
10 g sucrose
1 g NH$_4$Cl
0.2 g Mg$_2$SO$_4$ 7H$_2$O
0.01 g FeSO$_4$ 7H$_2$O
0.007 g MnSO$_4$ H$_2$O
EMM+G
80 ml EMM
20 ml 50 mM glyphosate
-adjust pH to 8.5

One particular strain, designated ATX1398, was selected due to its ability to grow in the presence of high glyphosate concentrations. ATX1398 was isolated from a sample of mushrooms. Approximately one gram of sample was added to 10 ml of EMM+G and incubated overnight at 25° C. 100 µl of this culture was added to a fresh tube containing 1 ml of EMM+G and incubated overnight. A loopful (1 µl) of this culture was used to inoculate fresh 1 ml of EMM+G. Strain ATX1398 was purified by re-streaking onto EMM agar (EMM with 15 g/L agar), and re-testing for ability to grow in the presence of glyphosate. Strain ATX1398 or strain JM101 were struck onto plates of EMM agar containing 5 mM glyphosate. The results of this test are shown in Table 1.

TABLE 1

Growth of ATHX1398 in the presence of glyphosate

| Strain | 0 mM | 5 mM glyphosate |
| --- | --- | --- |
| ATX1398 | +++ | +++ |
| JM101 (E. coli) | +++ | − |

EXAMPLE 2

Construction of Cosmid Libraries

Strain ATX1398 was grown in EMM, and cells were pelleted by centrifugation. Genomic DNA was extracted from ATX1 398, partially digested with the enzyme Sau3A I, ligated into a cosmid vector (Supercos 1 from Stratagene) and packaged into phage particles using techniques well known in the art. An aliquot of the phage was transfected into E. coli strain JM 101 (a strain known to be sensitive to glyphosate) and plated on LB agar medium containing 50 µg/ml kanamycin to select for colonies containing cosmids.

EXAMPLE 3

Isolation of Clones Conferring Glyphosate Resistance Upon E. coli

Approximately 700 kanamycin resistant colonies from genomic libraries of strain ATX1398 were replica plated onto LB-kanamycin agar, MOPS agar containing 50 µg/ml kanamycin and 2 mM glyphosate, and MOPS agar containing 50 µg/ml kanamycin and 5 mM glyphosate. Four clones grew in the presence of 2 mM glyphosate. Cosmid ATX1398(4) was observed to grow in the presence of 5 mM glyphosate. Cosmid DNA was purified from clone ATX1398(4) and retransformed into JM101 cells using standard techniques. All resulting colonies containing the intact cosmid were resistant to 5 mM glyphosate.

A second aliquot of packaged phage was transfected into JM101 cells and plated directly onto MOPS agar medium containing 50 mg/ml kanamycin and 2 mM glyphosate. Several glyphosate-resistant colonies were selected. One clone, cosmid ATX1398(11), was identified which conferred resistance. Restriction digest analysis of clone ATX1398(11) and comparison to restriction digest data from cosmid ATX1398 (4) showed that ATX1398(4) and ATX1398(11) are independent cosmid clones that contain overlapping sections of the same genomic region.

TABLE 2

Glyphosate resistance conferred by cosmid clones from ATHX1398

| Cosmid Clone | 0 mM | 2 mM glyphosate | 5 mM glyphosate |
| --- | --- | --- | --- |
| ATX1398(4) | +++ | +++ | +++ |
| ATX1398(11) | +++ | +++ | ND |
| Vector alone | +++ | — | − |

EXAMPLE 4

Identification of GRG-1 by Transposon Mutagenesis

To identify the gene(s) responsible for the glyphosate-resistance shown by cosmid ATX1398(4), DNA from this clone was mutagenized with transposable elements. In this method, one identifies clones that have suffered transposon insertions, and have lost the ability to confer glyphosate resistance. The location of the transposon insertions identifies the open reading frame responsible for the glyphosate resistance phenotype.

DNA from cosmid ATX1398(4) was subjected to in-vitro transposon mutagenesis using the Primer Island Kit (PE Biosystems) and transformed into E. coli strain XL1 Blue MRF' (Stratagene) by electroporation. Clones containing a transposon insertion were selected by plating on LB agar containing 50 µg/ml carbenicillin plus 50 µg/ml trimethoprim, then replica plated onto MOPS agar medium containing carbenicillin, trimethoprim and 2 mM glyphosate. Three colonies were identified which contained single transposon insertions and which did not grow in the presence of 2 mM glyphosate but did grow in its absence, indicating that the insertions were probably in or near the gene responsible for resistance to glyphosate. The sequence of the DNA surrounding the transposon insertions was determined using methods well known in the art. The transposon insertions were all found to reside in a single open reading frame, referred to herein as GRG-1.

Cosmid ATX1398(11) was also analyzed by in-vitro transposition and selective plating as described above.

TABLE 3

Mutation of GRG-1 by transposon insertion leads to loss of glyphosate resistance

| Clone | 0 mM | 2 mM glyphosate |
| --- | --- | --- |
| ATX1398(4) | +++ | +++ |
| ATX1398(4)::Tn5(4a17) | +++ | − |
| ATX1398(4)::Tn5(4a19) | +++ | − |
| ATX1398(11) | +++ | +++ |
| ATX1398(11)::Tn5(1) | +++ | − |
| ATX1398(11)::Tn5(2) | +++ | − |
| ATX1398(11)::Tn5(3) | +++ | − |
| Vector alone | +++ | − |

EXAMPLE 5

Sequence of GRG-1

The sequence of the GRG-1 open reading frame was determined in its entirety. Oligonucleotide primers were synthesized based on the sequence obtained from end sequences of transposon insertions. Sequencing reactions were performed using these oligonucleotide primers on clone ATX1398(4) DNA, and the resulting reactions were analyzed on an ABI 3700 automated sequencer, by methods known in the art. Overlapping sequencing reactions were assembled to generate the DNA sequence of the open reading frame which we have designated GRG-1.

Similarly, we determined the DNA sequence from multiple transposon insertions into clone ATX1398(11). These insertions had lost the ability to confer resistance to glyphosate (Table 3). DNA sequence from the region of the transposon insertions was identical to the sequence of GRG-1 obtained from ATX1398(4). Thus, clone ATX1398(11) also contains the GRG-1 gene, and insertions into this gene abolish the ability to confer glyphosate resistance.

EXAMPLE 6

Alignment of GRG-1 with Homologous Proteins

We compared the predicted amino acid sequence of GRG-1 to the non-redundant database of sequences maintained by the National Center for Biotechnology Information (NCBI), using the BLAST2 algorithm (Altschul et al. (1990) *J. Mol. Biol.* 215:403-410; Altschul et al. (1997) *Nucleic Acids Res.* 25:3389-3402; Gish and States (1993) *Nature Genet.* 3:266-272). BLAST algorithms compare a query sequence(s) for similarity to a database of known sequences and identifies sequences in the database(s) with highest scoring probability of similarity. The results of BLAST searches identified homology between the predicted GRG-1 open reading frame (SEQ ID NO:2) and several known proteins. The highest scoring amino acid sequences from this search were aligned with GRG-1 using ClustalW algorithm (Higgins et al. (1994) *Nucleic Acids Res.* 22:4673-4680) (as incorporated into the program ALIGNX module of the vector NTi Program Suite, Informax, Inc.). After alignment with ClustalW, the percent amino acid identity was assessed. The highest protein homology identified is a 34% amino acid identity to an EPSP synthase from *Clostridium acetobutylicum*. A similar search of the patent database at NCBI also identifies proteins with homology to GRG-1, though proteins identified in this search are less related to GRG-1. The protein with highest homology to GRG-1 in this search is the EPSP synthase of *H. influenzae* (SEQ ID NO:61 in U.S. Pat. No. 5,627,061), which is 25% identical to GRG-1.

The results of such searches show that GRG-1 encodes a novel protein. The protein encoded by GRG-1 has low homology to several members of the bacterial EPSP synthase enzyme family. Alignment of GRG-1 with several homologous proteins is shown in FIG. 1. Though not among the highest scoring results of BLAST searches using GRG-1, it is recognized that GRG-1 also shares homology with several sequences in U.S. Pat. No. 5,627,061 referred to therein as 'Class II' EPSP synthases, namely SEQ ID NO:3 (*Agrobacterium* sp. Strain CP4; 21% identity), SEQ ID NO:5 (*Achomobacter* sp. Strain LBAA), SEQ ID NO:7 (*Pseudomonas* sp. strain PG2982), SEQ ID NO:42 (*Bacillus subtilis;* 24% identity), and SEQ ID NO:44 (*Staphylococcus aureus*). Thus, GRG-1 shows homology to a broad class of EPSP synthases.

TABLE 4

Amino acid identity of GRG-1 to highest scoring EPSP synthases from a search of the translated NCBI "nr" database

| Organism | Amino Acid Identity to GRG-1 |
| --- | --- |
| *Clostridium acetobutylicum* | 34% |
| *Clostridium perfringens* | 34% |
| *Methanosarca mazei* | 32% |

TABLE 4-continued

Amino acid identity of GRG-1 to highest scoring EPSP synthases from a search of the translated NCBI "nr" database

| Organism | Amino Acid Identity to GRG-1 |
| --- | --- |
| *Aeropyrum pernix* | 31% |
| *Halobacterium* NRC-1 | 31% |
| *Methanosarcina acetivorans* | 31% |
| *Methanococcus jannushii* | 31% |
| *Methanopyrus kandleri* | 31% |
| *Fusobacterium nucleatum* | 29% |
| *Methanothermobacter thermautotrophicus* | 28% |
| *Archaeoglobus fulgidus* | 27% |
| *E. coli* | 25% |
| *Bacillus subtilis* | 24% |
| *Agrobacterium* sp. (Strain CP4) | 21% |

TABLE 5

Amino acid identity of GRG-1 to highest scoring proteins from a search of NCBI patent database

| Organism | SEQ ID NO. | Patent number | % amino acid Identity to GRG-1 |
| --- | --- | --- | --- |
| *H. influenzae* | 61 | US5627061 | 25% |
| *S. typhimurium* | 4 | EP0293358 | 25% |
| *S. typhimurium* | 3 | US4769061 | 25% |
| *E. coli* | 8 | US5627061 | 25% |
| *Salmonella galinarum* | 57 | US5627061 | 25% |
| *K. pneumoniae* | 59 | US5627061 | 25% |

The amino acid sequence of GRG-1 (SEQ ID NO:2) was aligned with the predicted amino acid sequences of five EPSP synthase enzymes obtained from GenBank using the ClustalW algorithm. The five sequences aligned to GRG-1 represent EPSP synthase proteins from a diverse cross section of organisms; the monocotyledonous plant *Zea mays* (GenBank Accession No. X63374.1) the dicotyledonous plant *Arabidopsis thaliana* (GenBank Accession No. NM_103780.2), the bacteria *E. coli* (GenBank Accession No. NC_000913.1) and *Agrobacterium tumifaciens* (GenBank Accession No. Q9R4E4) and the yeast *Saccharomyces cerevisiae* (a portion of GenBank Accession No. NC_00136.2). The alignment is shown in FIG. 3. This alignment, as well as the alignments shown in FIG. 1 and FIG. 2, identifies several amino acids that are conserved among the EPSP synthases shown and GRG-1. These residues are listed in Table 6.

TABLE 6

Alignment of GRG-1 with the five related proteins from FIG. 3

| Amino Acid | Position in GRG1 | Position in Alignment |
| --- | --- | --- |
| P | 17 | 101 |
| K | 20 | 104 |
| S | 21 | 105 |
| R | 25 | 109 |
| G | 35 | 119 |
| D | 47 | 131 |
| G | 76 | 163 |
| G | 87 | 180 |
| R | 94 | 187 |
| R | 118 | 216 |
| P | 119 | 217 |
| L | 127 | 225 |
| G | 131 | 229 |
| P | 142 | 242 |

TABLE 6-continued

Alignment of GRG-1 with the five related proteins from FIG. 3

| Amino Acid | Position in GRG1 | Position in Alignment |
|---|---|---|
| S | 162 | 265 |
| T | 196 | 299 |
| F | 203 | 306 |
| G | 204 | 307 |
| D | 237 | 340 |
| S | 239 | 342 |
| L | 245 | 348 |
| L | 274 | 380 |
| D | 307 | 425 |
| A | 316 | 434 |
| T | 323 | 448 |
| K | 334 | 459 |
| E | 335 | 460 |
| R | 338 | 463 |
| G | 350 | 475 |
| D | 378 | 513 |
| H | 379 | 514 |
| R | 380 | 515 |
| A | 382 | 517 |
| M | 383 | 518 |
| P | 509 | 553 |

EXAMPLE 7

Expression of GRG-1 in E. Coli

GRG-1 is expressed in E. coli in the following way. First, one designs oligonucleotide primers that are homologous to each end of the gene, such that a PCR reaction (by one skilled in the art) will result in a DNA that contains essentially all of the coding region of GRG-1. This PCR product may contain additional signal regions, such as a ribosome binding site, promoter, or sites recognized by restriction enzymes, etc. The resulting PCR reaction is cloned into a vector such as pQE60 (Invitrogen) that allows inducible protein expression. The PCR product, and cloning experiment are designed such that the resulting clone contains a proper ribosome binding site and ATG (or GTG) start codon positioned relative to the bacterial promoter (such as the Tac promoter) of the vector. The GRG-1 expressing clone is then constructed by inserting the PCR product into the expression vector by methods known in the art. The resulting clone is placed into an E. coli cell (for example by electroporation) and colonies containing the clone identified by methods known in the art, such as selecting for an antibiotic resistance gene present in the plasmid (such as an ampicillin resistance gene). GRG-1 expression is tested by plating cells onto media containing an inducer of GRG-1 transcription (such as IPTG), and either 0 mM, 2 mM, or 5 mM glyphosate, and assessing the ability of clones expressing GRG-1 to grow on glyphosate-containing media relative to vector controls. In some instances, it will be preferable to perform this experiment using substantially higher concentrations of glyphosate, such as 10 mM, 20 mM or even as much as 50 mM. This is especially true when the expressed clones produce substantial quantities of enzyme. In these cases, high concentrations of glyphosate may be required to achieve sensitivity to glyphosate with control genes, such as the wild-type aroA of E. coli. One can quickly determine the preferred concentration of glyphosate by plating clones expressing GRG-1 and clones expressing E. coli aroA individually onto plates that (1) allow protein expression (for example by adding IPTG to induce transcription of lac-based promoters) and (2) contain differing amounts of glyphosate (for example, 0-50 mM in 5 mM increments).

EXAMPLE 8

Test of Glyphosate Resistance of GRG-1 Expressing Clones vs aroA

Strains engineered to express either GRG-1 or the wild-type E. coli aroA were engineered as described in the following way. A customized expression vector, pPEH304Cm was constructed. The essential features of pPEH304Cm are the origin of replication from pBR322, a chloramphenicol acetyl transferase gene (for selection and maintenance of the plasmid), the lacI gene, the Ptac promoter and the rrnB transcriptional terminator. The GRG-1 open reading frame was amplified as described in Example 7. The oligonucleotides for PCR amplification of GRG-1 were designed to overlap the start codon of GRG-1, such that the resulting PCR product resulted in conversion of the native GTG start codon of GRG-1 to an ATG codon. The aroA open reading frame was amplified by PCR from E. coli strain XL1 Blue MRF' (Stratagene). During PCR, restriction sites were added to facilitate cloning into pPEH304Cm.

The PCR products for GRG-1 and aroA were cloned into the expression vector pPEH304Cm to yield the plasmids pPEH306 and pPEH307, respectively, and transformed into E. coli XL1 Blue MRF'. Correct clones were identified by standard methods known in the art. The sequence of the GRG-1 and aroA open reading frames in expression clones in pPEH306 and pPEH307 were confirmed by DNA sequencing.

Strains were grown to saturation (overnight) in Luria Broth (Sambrook and Russell, 2001, supra) then diluted 1:100 in M9 liquid medium (recipe) containing 0 to 30 mM glyphosate, and supplemented with 10 g glucose, 10 mg Thiamine-HCl and 25 mg L-Proline. High level transcription from the Ptac promoter was stimulated by including 0.1 mM IPTG in a subset of the cultures (noted as +IPTG in Table 7).

5× M9 media
30 g $Na_2HPO_4$
51 g $KH_2PO_4$
5 g $NH_4Cl$
2.5 g NaCl
15 mg $CaCl_2$ Each culture was grown in a 3 ml tube at 37° C. on a culture wheel. There were three replicate tubes of each treatment. After 8 hours of growth, 310 microliters of culture was withdrawn and placed into a 96-well plate. The absorbance of the culture at 600 nm was measured on a Spectramax 96 well plate reader. The experiment was performed in triplicate, and the values in Table 7 reflect the means of three cultures.

TABLE 7

Resistance of GRG-1 expressing strains to high levels of glyphosate in Luria Broth at 8 hours

| | Glyphosate Concentration (mM) | | | | |
|---|---|---|---|---|---|
| Construct | 0 | 5 | 10 | 20 | 30 |
| Vector + IPTG | 0.078 | 0.045 | 0.040 | 0.030 | 0.044 |
| GRG-1 + IPTG | 0.100 | 0.104 | 0.117 | 0.125 | 0.135 |
| aroA + IPTG | 0.075 | 0.068 | 0.063 | 0.056 | 0.052 |
| Vector | 0.092 | 0.039 | 0.039 | 0.042 | 0.043 |
| GRG-1 | 0.092 | 0.102 | 0.110 | 0.112 | 0.104 |
| aroA | 0.095 | 0.048 | 0.046 | 0.047 | 0.048 |

The data in Table 7 shows that GRG-1 encodes resistance to a high level of glyphosate, and allow not only survival, but growth of E. coli in the presence of 30 mM glyphosate. In contrast, growth of cells expressing aroA is inhibited by glyphosate concentrations of 10 mM and higher.

In addition, these strains engineered to express either GRG-1 or the wild-type E. coli aroA, were tested in another minimal media, M63, with glyphosate concentrations up to 150 mM. 1× M63 was supplemented with 10 g glucose, 10 mg Thiamine-HCl and 25 mg L-Proline. The strains were grown to saturation (overnight) in Luria Broth (Sambrook and Russell, 2001, supra) then washed two times in M63 media (adapted from Current Protocols in Molecular Biology, Greene Publishing and Wiley-Interscience, New York) before being diluted 1:100 in fresh M63 liquid medium containing 0 to 150 mM glyphosate. High level transcription from the Ptac promoter was stimulated by including 0.1 mM IPTG all of the cultures.

5× M63
68 g $KH_2PO_4$
10 g $(NH_4)_2SO_4$
2.5 mg $FeSO_4$-$7H_2O$
12 mg $MgCl_2$

Each culture was grown in 2 mls of media in 10 ml tubes at 37° C. in a shaker. At 24 hours, 300 microliters of the culture was withdrawn and placed into a 96-well assay plate. The absorbance of the culture at 600 nm was measured on a Spectromax 96 well plate reader. The values in Table 8 reflect this experiment at 24 hours (NT not tested).

TABLE 8

Resistance of GRG-1 expressing strains to high levels of glyphosate in M63 at 24 hours

| | Glyphosate Concentration | | | | |
|---|---|---|---|---|---|
| Construct | 0 | 5 | 30 | 60 | 150 |
| Vector + IPTG | 0.5695 | 0.032 | 0.0323 | 0.0325 | 0.045 |
| GRG-1 + IPTG | 0.4943 | 0.7192 | 0.7884 | 0.789 | 0.951 |
| aroA + IPTG | 0.5982 | 0.1209 | 0.0276 | 0.0298 | NT |

EXAMPLE 9

GRG-1 Complements an aroA Mutation in E. coli XL-1 MRF' Cells

Using PCR and recombination methods known in the art, and outlined by Datsenko and Wanner (Datsenko and Wanner (2000) Proc. Natl. Acad. Sci. U.S.A. 97:6640-6645), an aroA knockout strain of E. coli XL-1 MRF' (Stratagene) was created. This system is based on the Red system which allows for chromosomal disruptions of targeted sequences. The aroA gene codes for EPSP synthase, the target enzyme for glyphosate. Therefore, by disrupting the gene, complementation of EPSP synthase activity could be screened for.

Using this system, 1067 bases of the 1283 bases of the aroA coding region were disrupted. The deletion of the aroA coding region was confirmed by PCR, and by complementing the deletion with a wild-type aroA gene as described below.

EPSP synthase catalyzes the sixth step in the biosynthesis of aromatic amino acids in microbes and plants, therefore minimal media that lacks aromatic amino acids do not support growth of organisms lacking an EPSP synthase (Pittard and Wallace (1966) J. Bacteriol. 91:1494-508).

The aroA knockout generated above grew on LB media but did not grow on M63 minimal media. Furthermore, the knockout did grow on M63 media supplemented with phenylalanine, tryptophan, and tyrosine. These results indicate that the aroA gene had been disrupted. Additionally, complementation was tested to ensure that the gene function could be restored. Electrocompetent cells of the knockout aroA strain were made by traditional methods. Clone pPEH307, the expression vector containing the aroA gene, was transformed into the knockout cells and plated on LB media, M63, and M63 with amino acid supplements. The resulting transformant grew on all three media types. To test the ability of GRG-1 to complement aroA, plasmid pPEH306 (the expression vector containing GRG-1) was transformed into the aroA knockout cells and these cells were plated on the three types of media described above. The resulting transformant grew on all three media types. As a control, the vector pPEH304 was transformed into the aroA knockout cells and plated on LB, M63, and M63 with amino acid supplements. These cells grew on LB and M63 supplemented with aromatic amino acids, but did not grow on M63 alone. This indicates that the expression vector alone did not have the necessary components to complement the aroA mutation.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. An isolated polypeptide comprising the amino acid sequence of SEQ ID NO:2.

2. An isolated glyphosate resistance protein having at least 95% sequence identity to the amino acid sequence of SEQ ID NO:2.

* * * * *

SEQUENCE LISTING

```
<160> NUMBER OF SEQ ID NOS: 2

<210> SEQ ID NO 1
<211> LENGTH: 1398
<212> TYPE: DNA
<213> ORGANISM: Enterobacteriaceae
<220> FEATURE:
<221> NAME/KEY: CDS
<222> LOCATION: (103)...(1398)

<400> SEQUENCE: 1
```

-continued

```
aaaaaaggaa atgaactatg tgttgctgga aaaagtaggg aagggagtgg tgaagagtat      60
tccactggtt caattagaaa aaatcattca aggattacca aa gtg aaa gta aca        114
                                                Met Lys Val Thr
                                                  1 ata cag ccc gga gat ctg act gga att atc cag tca ccc gct tca aaa      162
Ile Gln Pro Gly Asp Leu Thr Gly Ile Ile Gln Ser Pro Ala Ser Lys
  5              10                  15                  20 agt tcg atg cag cga gct tgt gct gct gca ctg gtt gca aaa gga ata      210
Ser Ser Met Gln Arg Ala Cys Ala Ala Ala Leu Val Ala Lys Gly Ile
             25                  30                  35 agt gag atc att aat ccc ggt cat agc aat gat gat aaa gct gcc agg      258
Ser Glu Ile Ile Asn Pro Gly His Ser Asn Asp Asp Lys Ala Ala Arg
         40                  45                  50 gat att gta agc cgg ctt ggt gcc agg ctt gaa gat cag cct gat ggt      306
Asp Ile Val Ser Arg Leu Gly Ala Arg Leu Glu Asp Gln Pro Asp Gly
             55                  60                  65 tct ttg cag ata aca agt gaa ggc gta aaa cct gtc gct cct ttt att      354
Ser Leu Gln Ile Thr Ser Glu Gly Val Lys Pro Val Ala Pro Phe Ile
     70                  75                  80 gac tgc ggt gaa tct ggt tta agt atc cgg atg ttt act ccg att gtt      402
Asp Cys Gly Glu Ser Gly Leu Ser Ile Arg Met Phe Thr Pro Ile Val
 85                  90                  95                 100 gcg ttg agt aaa gaa gag gtg acg atc aaa gga tct gga agc ctt gtt      450
Ala Leu Ser Lys Glu Glu Val Thr Ile Lys Gly Ser Gly Ser Leu Val
                105                 110                 115 aca aga cca atg gat ttc ttt gat gaa att ctt ccg cat ctc ggt gta      498
Thr Arg Pro Met Asp Phe Phe Asp Glu Ile Leu Pro His Leu Gly Val
            120                 125                 130 aaa gtt aaa tct aac cag ggt aaa ttg cct ctc gtt ata cag ggg cca      546
Lys Val Lys Ser Asn Gln Gly Lys Leu Pro Leu Val Ile Gln Gly Pro
        135                 140                 145 ttg aaa cca gca gac gtt acg gtt gat ggg tcc tta agc tct cag ttc      594
Leu Lys Pro Ala Asp Val Thr Val Asp Gly Ser Leu Ser Ser Gln Phe
150                 155                 160 ctt aca ggt ttg ttg ctt gca tat gcg gcc gca gat gca agc gat gtt      642
Leu Thr Gly Leu Leu Leu Ala Tyr Ala Ala Ala Asp Ala Ser Asp Val
165                 170                 175                 180 gcg ata aaa gta acg aat ctc aaa agc cgt ccg tat atc gat ctt aca      690
Ala Ile Lys Val Thr Asn Leu Lys Ser Arg Pro Tyr Ile Asp Leu Thr
                185                 190                 195 ctg gat gtg atg aag cgg ttt ggt ttg aag act ccc gag aat cga aac      738
Leu Asp Val Met Lys Arg Phe Gly Leu Lys Thr Pro Glu Asn Arg Asn
            200                 205                 210 tat gaa gag ttt tat ttc aaa gcc ggg aat gta tat gat gaa acg aaa      786
Tyr Glu Glu Phe Tyr Phe Lys Ala Gly Asn Val Tyr Asp Glu Thr Lys
        215                 220                 225 atg caa cga tac acc gta gaa ggc gac tgg agc ggt ggt gct ttt tta      834
Met Gln Arg Tyr Thr Val Glu Gly Asp Trp Ser Gly Gly Ala Phe Leu
230                 235                 240 ctg gta gcg ggg gct att gcc ggg ccg atc acg gta aga ggt ttg gat      882
Leu Val Ala Gly Ala Ile Ala Gly Pro Ile Thr Val Arg Gly Leu Asp
245                 250                 255                 260 ata gct tcg acg cag gct gat aaa gcg atc gtt cag gct ttg atg agt      930
Ile Ala Ser Thr Gln Ala Asp Lys Ala Ile Val Gln Ala Leu Met Ser
                265                 270                 275 gcg aac gca ggt att gcg att gat gca aaa gag atc aaa ctt cat cct      978
Ala Asn Ala Gly Ile Ala Ile Asp Ala Lys Glu Ile Lys Leu His Pro
            280                 285                 290 gct gat ctc aat gca ttt gaa ttt gat gct act gat tgc ccg gat ctt     1026
```

-continued

```
Ala Asp Leu Asn Ala Phe Glu Phe Asp Ala Thr Asp Cys Pro Asp Leu
        295                 300                 305 ttt ccg cca ttg gtt gct ttg gcg tct tat tgc aaa gga gaa aca aag      1074
Phe Pro Pro Leu Val Ala Leu Ala Ser Tyr Cys Lys Gly Glu Thr Lys
    310                 315                 320 atc aaa ggc gta agc agg ctg gcg cat aaa gaa agt gac aga gga ttg      1122
Ile Lys Gly Val Ser Arg Leu Ala His Lys Glu Ser Asp Arg Gly Leu
325                 330                 335                 340 acg ctg cag gac gag ttc ggg aaa atg ggt gtt gaa atc cac ctt gag      1170
Thr Leu Gln Asp Glu Phe Gly Lys Met Gly Val Glu Ile His Leu Glu
                345                 350                 355 gga gat ctg atg cgc gtg atc gga ggg aaa ggc gta aaa gga gct gaa      1218
Gly Asp Leu Met Arg Val Ile Gly Gly Lys Gly Val Lys Gly Ala Glu
            360                 365                 370 gtt agt tca agg cac gat cat cgc att gcg atg gct tgc gcg gtg gct      1266
Val Ser Ser Arg His Asp His Arg Ile Ala Met Ala Cys Ala Val Ala
        375                 380                 385 gct tta aaa gct gtg ggt gaa aca acc atc gaa cat gca gaa gcg gtg      1314
Ala Leu Lys Ala Val Gly Glu Thr Thr Ile Glu His Ala Glu Ala Val
    390                 395                 400 aat aaa tcc tac ccg gat ttt tac agc gat ctt aaa caa ctt ggc ggt      1362
Asn Lys Ser Tyr Pro Asp Phe Tyr Ser Asp Leu Lys Gln Leu Gly Gly
405                 410                 415                 420 gtt gta tct tta aac cat caa ttt aat ttc tca tga                      1398
Val Val Ser Leu Asn His Gln Phe Asn Phe Ser  *
                425                 430

<210> SEQ ID NO 2
<211> LENGTH: 431
<212> TYPE: PRT
<213> ORGANISM: Enterobacteriaceae

<400> SEQUENCE: 2

Met Lys Val Thr Ile Gln Pro Gly Asp Leu Thr Gly Ile Leu Gln Ser
 1               5                  10                  15

Pro Ala Ser Lys Ser Ser Met Gln Arg Ala Cys Ala Ala Ala Leu Val
            20                  25                  30

Ala Lys Gly Ile Ser Glu Ile Ile Asn Pro Gly His Ser Asn Asp Asp
        35                  40                  45

Lys Ala Ala Arg Asp Ile Val Ser Arg Leu Gly Ala Arg Leu Glu Asp
    50                  55                  60

Gln Pro Asp Gly Ser Leu Gln Ile Thr Ser Glu Gly Val Lys Pro Val
65                  70                  75                  80

Ala Pro Phe Ile Asp Cys Gly Glu Ser Gly Leu Ser Ile Arg Met Phe
                85                  90                  95

Thr Pro Ile Val Ala Leu Ser Lys Glu Val Thr Ile Lys Gly Ser
            100                 105                 110

Gly Ser Leu Val Thr Arg Pro Met Asp Phe Phe Asp Glu Ile Leu Pro
        115                 120                 125

His Leu Gly Val Lys Val Lys Ser Asn Gln Gly Lys Leu Pro Leu Val
    130                 135                 140

Ile Gln Gly Pro Leu Lys Pro Ala Asp Val Thr Val Asp Gly Ser Leu
145                 150                 155                 160

Ser Ser Gln Phe Leu Thr Gly Leu Leu Leu Ala Tyr Ala Ala Ala Asp
                165                 170                 175

Ala Ser Asp Val Ala Ile Lys Val Thr Asn Leu Lys Ser Arg Pro Tyr
            180                 185                 190
```

-continued

```
Ile Asp Leu Thr Leu Asp Val Met Lys Arg Phe Gly Leu Lys Thr Pro
        195                 200                 205

Glu Asn Arg Asn Tyr Glu Glu Phe Tyr Phe Lys Ala Gly Asn Val Tyr
        210                 215                 220

Asp Glu Thr Lys Met Gln Arg Tyr Thr Val Glu Gly Asp Trp Ser Gly
225                 230                 235                 240

Gly Ala Phe Leu Leu Val Ala Gly Ala Ile Ala Gly Pro Ile Thr Val
                245                 250                 255

Arg Gly Leu Asp Ile Ala Ser Thr Gln Ala Asp Lys Ala Ile Val Gln
                260                 265                 270

Ala Leu Met Ser Ala Asn Ala Gly Ile Ala Ile Asp Ala Lys Glu Ile
                275                 280                 285

Lys Leu His Pro Ala Asp Leu Asn Ala Phe Glu Phe Asp Ala Thr Asp
        290                 295                 300

Cys Pro Asp Leu Phe Pro Pro Leu Val Ala Leu Ala Ser Tyr Cys Lys
305                 310                 315                 320

Gly Glu Thr Lys Ile Lys Gly Val Ser Arg Leu Ala His Lys Glu Ser
                325                 330                 335

Asp Arg Gly Leu Thr Leu Gln Asp Glu Phe Gly Lys Met Gly Val Glu
                340                 345                 350

Ile His Leu Glu Gly Asp Leu Met Arg Val Ile Gly Gly Lys Gly Val
                355                 360                 365

Lys Gly Ala Glu Val Ser Ser Arg His Asp His Arg Ile Ala Met Ala
        370                 375                 380

Cys Ala Val Ala Ala Leu Lys Ala Val Gly Glu Thr Thr Ile Glu His
385                 390                 395                 400

Ala Glu Ala Val Asn Lys Ser Tyr Pro Asp Phe Tyr Ser Asp Leu Lys
                405                 410                 415

Gln Leu Gly Gly Val Val Ser Leu Asn His Gln Phe Asn Phe Ser
                420                 425                 430
```